United States Patent [19]

McGregor et al.

[11] 4,066,634

[45] Jan. 3, 1978

[54] PURIFICATION OF SYNTHETIC SOMATOSTATIN

[75] Inventors: William H. McGregor, Malvern; Joseph J. Dougherty, Drexel Hill, both of Pa.

[73] Assignee: American Home Products Corporation, New York, N.Y.

[21] Appl. No.: 719,304

[22] Filed: Aug. 31, 1976

[51] Int. Cl.$^2$ .................... C07C 103/52; A61K 37/00
[52] U.S. Cl. .............................. 260/112.5 S; 424/177
[58] Field of Search ................................... 260/112.5 S

[56] References Cited

U.S. PATENT DOCUMENTS

| 2,992,164 | 7/1961 | Moses | 260/112.5 R |
| 3,221,008 | 11/1965 | Wolf et al. | 260/112.5 R |
| 3,259,617 | 7/1966 | Sheehan | 260/112.5 R |
| 3,331,828 | 7/1967 | Inamine et al. | 260/112.5 R |
| 3,862,925 | 1/1975 | Sarantakis et al. | 260/112.5 S |
| 3,929,758 | 12/1975 | Hughes et al. | 260/112.5 S |

OTHER PUBLICATIONS

J. A. C. S. 96, (1974), pp. 2986–2992.

*Primary Examiner*—Delbert R. Phillips
*Attorney, Agent, or Firm*—Richard K. Jackson

[57] ABSTRACT

High speed liquid chromatography of synthetically produced somatostatin yields somatostatin free from structural artifacts.

2 Claims, No Drawings

PURIFICATION OF SYNTHETIC SOMATOSTATIN

BACKGROUND OF THE INVENTION

The structure of natural somatostatin was first elucidated by Brazeau et al., Science, 179, 77 (1973) as the cyclic tetradecapeptide H-Ala-Gly-Cys-Lys-Asn-Phe-Phe-Trp-Lys-Thr-Phe-Thr-Ser-Cys-OH Somatostatin has been synthetically produced by the solution method (Sarantakis et al., Biochem. Biophys. Res. Comm., Vol. 54. No. 1, pp. 234–238 (1973) and Immer et al., Helv. Chem Acta, 57, No. 81, pp. 730–734 (1974) and the solid phase method (Rivier, J.A.C.S. 96, 9, pp. 2986–2992 (1974).

DESCRIPTION OF THE INVENTION

We have now discovered that both the solid phase and solution techniques for preparation of Somatostatin usually, but not always, yield a product containing one or more structural artifacts of the desired product. Purification techniques employed routinely heretofore in the work-up of Somatostatin do not remove these impurities to yield pure Somatostatin.

In accordance with this invention, there is provided a process for producing chromatographically pure Somatostatin, which process comprises passing an aqueous solution of impure synthetically produced somatostatin through a packed column of a weakly acidic ion exchange resin containing ammonium carboxylate functional groups with the aid of an ammonium hydroxide/ammonium acetate eluant in a volume/volume ratio of 1 to 9 : 1 and collecting the somatostatin containing fraction of eluate.

The eluate fraction containing pure somatostatin follows the elution of the structural artifacts through the column of exchange resin to appear as the main elution product.

Although the structural artifacts produced with somatostatin possess the same biological activity as somatostatin and need not be removed from somatostatin prior to use, from an analytical standpoint it is desirable to be able to isolate and characterize pure somatostatin for production purposes.

Pure cyclic somatostatin was prepared by the following method:

To 20 Grams of Merrifield Resin containing 0.5 milliequivalents per gram of (t-butyloxycarbonyl)cysteine(p-methoxybenzyl) prepared by the method of Monahan et al., was coupled (t-butyloxycarbonyl)-L-Thr(Obenzyl)-L-Ser(Obenzyl)-OH using dicyclohexylcarbodiimide and 1-hydroxybenzotriazole followed by (t-butyloxycarbonyl)-L-Thr(Obenzyl)-Phe-Oh using dicyclohexylcarbodiimide and 1-hydroxybenzotrizole. Subsequently the other amino acids of SRIF were incorporated into the polypeptide as individual amino acids. Asparagine was used as the t-butyloxycarbonyl-p-nitrophenyl ester.

10 Grams of the SRIF-resin product was cleaved with HF in the usual fashion (3.39 grams) and cyclized in aerated water. The aqueous solution was then stored for 3 days at 4° C., lyophyllized to give 0.86 grams of product. The 0.86 grams of cyclic SRIF was partitioned on Sephadex G25F using butanolglacial acetic acid-water 4:1:5 and collected in 4 milliliter fractions. The following fractions were pooled:

| TUBES | | |
|---|---|---|
| 35 – 55 | 111 milligrams | 163 – 1 |
| 56 – 75 | 121 | 163 – 2 |
| 76 – 95 | 120 | 163 – 3 |
| 96 – 120 | | 163 – 4 |

Analytically pure standard samples of somatostatin were then prepared by injecting 25 microliters of a crude aqueous solution containing 1 milligram per milliliter of the cyclic tetradecapeptide from each of the pooled fractions onto a stainless steel column (⅜ × 36 inches) packed with Bio-Rex 70 (a weakly acidic resin containing carboxylic acid exchange groups on an acrylic polymer lattice) in the ammonium cycle. The column was eluted with an 80/20 mixture by volume of 0.05 M ammonium hydroxide/ammonium acetate (pH 9.1) at a flow rate of 2.0 milliliters per minute. The elution was monitored with a Waters Associates Liquid Chromatograph model ALC-202 equipped with a U.V. detector to monitor absorption at 254 nanometers. The initially eluting impurities present a retention time of about 5.4 while the main body of somatostatin had a retention time of about 13.0, while the ratio of the area of somatostatin to impurities increased from 0.16 to 1.08 running from fraction I to fraction IV.

The resolving capacity of the ion exchange resin was established by re-chromatographing the somatostatin fraction by the same high speed liquid chromatographic system used in the original fractionation, to obtain a symmetrical single chromatographic peak denoting a pure material.

Repetition of the high speed liquid chromatographic fractionation technique of this invention with somatostatin obtained by the classic solution preparatory method gave the same results, with a body of impurities being removed from the column ahead of the main body of pure somatostatin.

In actual production practice, the crude sample of somatostatin is dissolved in water to afford an aqueous solution containing about 0.5 gram per milliliter. The sample is injected via a loop injector onto Bio-Rex 70 (a weakly acidic resin containing carboxylic acid exchange groups on an acrylic polymer lattice) on the ammonium cycle, packed in a stainless steel column (1 × 36 inches). The eluant employed is an 80/20 mixture by volume of 0.05M $NH_4OH/CH_3CO_2NH_4$ (pH 9.1). The flow rate through the column is about 6.9 milliliters per minute. The elution was followed with a U.V. detector set to monitor absorption at 254 nanometers at a range setting of 1.28 millivolts. The main somatostatin fraction following the elution of impurities is collected and lyophilized.

The process of this invention has been repeatedly performed with mixtures of from 0.01 M to 0.2 M $NH_4OH/CH_3CO_2NH_4$ in varying ratios of from 1 to 9 parts $NH_4OH$ to 1 part $CH_3CO_2NH_4$ with equal success.

What is claimed is:
1. A process for producing chromatographically pure somatostatin which comprises
   a. passing an aqueous solution of impure, synthetically produced somatostatin through a weakly acidic ion exchange resin containing ammonium carboxylate functional groups, with an ammonium hydroxide-ammonium acetate eluant in a volume/volume ratio of 1 to 9 : 1 and
   b. collecting the somatostatin containing fraction of eluate.
2. The process of claim 1 in which said somatostatin containing fraction of eluate follows the elution of structural artifacts through said resin.